(12) United States Patent
Hinkle et al.

(10) Patent No.: US 10,402,924 B2
(45) Date of Patent: Sep. 3, 2019

(54) SYSTEM AND METHOD FOR REMOTE MANAGEMENT AND DETECTION OF CLIENT COMPLICATIONS

(71) Applicant: Interactive Intelligence, Inc., Indianapolis, IN (US)

(72) Inventors: Zachary Hinkle, Westfield, IN (US); Jason Andrew Loucks, DeForest, WI (US); Logan H. Weilenman, Greenwood, IN (US); Ryan Collins, Indianapolis, IN (US)

( * ) Notice: Subject to any disclaimer, the term of this patent is extended or adjusted under 35 U.S.C. 154(b) by 681 days.

(21) Appl. No.: 14/188,921

(22) Filed: Feb. 25, 2014

(65) Prior Publication Data
US 2014/0244285 A1 Aug. 28, 2014

Related U.S. Application Data

(60) Provisional application No. 61/769,829, filed on Feb. 27, 2013.

(51) Int. Cl.
*G06F 19/00* (2018.01)
*G06Q 50/00* (2012.01)
(Continued)

(52) U.S. Cl.
CPC ......... *G06Q 50/22* (2013.01); *G06F 19/3418* (2013.01); *G06Q 10/0633* (2013.01); *G16H 50/20* (2018.01); *G16H 10/60* (2018.01)

(58) Field of Classification Search
CPC ........ G06Q 50/22; G06Q 50/24; G06Q 40/08; G06Q 10/10; G06Q 19/322; A61N 1/08; G06F 17/30; G06F 19/30; G06F 19/32; G06F 19/321; G06F 19/324; G06F 19/325; G06F 19/326; G06F 19/328; G06F 19/34; G06F 19/3418; G06F 19/3456; G06F 19/3462; G06F 19/3468; G06F 19/3475; G06F 19/3481; G06F 19/36; G16H 10/00; G16H 10/20; G16H 10/40; G16H 10/60; G16H 10/65; G16H 15/00; G16H 20/00; G16H 20/10; G16H 20/13; G16H 20/17; G16H 20/30; G16H 20/40; G16H 20/60; G16H 20/70; G16H 20/90; G16H 30/00; G16H 30/20; G16H 30/40; G16H 40/00;
(Continued)

(56) References Cited

U.S. PATENT DOCUMENTS

| 4,941,178 | A | * | 7/1990 | Chuang | G10L 15/065 704/241 |
| 6,032,119 | A | * | 2/2000 | Brown | G06F 19/325 177/25.19 |
| 7,769,600 | B2 | | 8/2010 | Iliff | |
| 8,066,640 | B2 † | | 11/2011 | Angelides | |

(Continued)

OTHER PUBLICATIONS

International Search Report dated Jul. 30, 2014 in related foreign application PCT/US/14/18169 filed Feb. 25, 2014.

*Primary Examiner* — Tran N Nguyen

(57) ABSTRACT

A system and method are presented for relationship management workflow processes. At least one embodiment may apply to process automation to health care. More specifically, the system and method may be applied to patient management of healthcare, such as the management of Diabetes or other medical conditions. Other embodiments may apply to process automation in other areas utilizing management workflow software.

6 Claims, 8 Drawing Sheets

(51) Int. Cl.
  *G06Q 10/06* (2012.01)
  *G06Q 50/22* (2018.01)
  *G16H 50/20* (2018.01)
  *G16H 10/60* (2018.01)
  *G06Q 10/00* (2012.01)

(58) Field of Classification Search
  CPC ........ G16H 40/20; G16H 40/40; G16H 40/60;
      G16H 40/63; G16H 40/67; G16H 50/00;
      G16H 50/20; G16H 50/30; G16H 50/50;
      G16H 50/70; G16H 50/80; G16H 70/00;
      G16H 70/20; G16H 70/14; G16H 70/60;
      G16H 80/00
  See application file for complete search history.

(56) References Cited

U.S. PATENT DOCUMENTS

| | | | |
|---|---|---|---|
| 8,812,244 B2 † | 8/2014 | Angelides | |
| 8,825,786 B1 † | 9/2014 | Webb | |
| 2007/0141539 A1 † | 6/2007 | Lemieux | |
| 2007/0293772 A1 * | 12/2007 | Bardy | A61B 5/0031 600/481 |
| 2010/0010832 A1 * | 1/2010 | Boute | G06F 19/3418 705/3 |
| 2010/0191075 A1 † | 7/2010 | Angelides | |
| 2011/0184752 A1 | 7/2011 | Ray et al. | |
| 2013/0003943 A1 * | 1/2013 | Munns | H04M 3/5166 379/88.01 |
| 2013/0046543 A1 † | 2/2013 | Kitchens | |
| 2013/0078601 A1 † | 3/2013 | Angelides | |

\* cited by examiner
† cited by third party

CLIENT INFORMATION

| | 600a | 600b | 600c |
|---|---|---|---|
| 605 Date/Time Created | 1/5/2013 8:00:00 AM | 1/5/2013 10:32:00 AM | 1/7/2013 2:53:00 PM |
| 610 User ID | 5678 | 23504 | 85213 |
| 615 Date of Birth | 5/10/1950 | 8/6/1944 | 1/4/1979 |
| 620 Title | Mrs. | Dr. | Mr. |
| 625 First Name | Suzie | Jim | Brian |
| 630 Last Name | Leck | Doe | Parsons |
| 635 Phone Number | 555-555-5555 | 555-555-6645 | 555-555-1235 |
| 640 Email | suzie.leck234@isp.com | none | captain@isp.com |
| 645 Gender | F | M | M |
| 650 Smoker | Yes | N | N |
| 655 Occupation | Homemaker | Retired | Skilled Trade |
| 660 State | AZ | NV | AK |
| 665 Gross Annual Income | $50,000 | $0 | $45,000 |

CLIENT READINGS

|  | 700a | 700b | 700c |
|---|---|---|---|
| 705 UserID | 5678 | 23504 | 85213 |
| 710 Reading | 300 | 150 | 129 |
| 715 Reading Type | Glucose | Glucose | HDL |
| 720 Time of Reading | 1/5/2013 7:59:00 AM | 1/4/2013 5:17:00 PM | 1/7/2013 2:52:00 PM |
| 725 Record Created | 1/5/2013 8:00:00 AM | 1/5/2013 10:32:00 AM | 1/7/2013 2:53:00 PM |

Fig. 7

SYSTEM AND METHOD FOR REMOTE MANAGEMENT AND DETECTION OF CLIENT COMPLICATIONS

CROSS-REFERENCE TO RELATED APPLICATIONS

This application claims the benefit of U.S. Provisional Application No. 61/769,829, filed Feb. 27, 2013, and titled SYSTEM AND METHOD FOR REMOTE MANAGEMENT AND DETECTION OF CLIENT COMPLICATIONS. The disclosure of the prior application is considered part of an is incorporated by reference in the disclosure of this application.

BACKGROUND

The present invention generally relates to telecommunications systems and methods, as well as process automation. More particularly, the present invention pertains to management workflow software.

SUMMARY

A system and method are presented for relationship management workflow processes. At least one embodiment may apply to healthcare process automation. More specifically, the system and method may be applied to patient management of healthcare, such as the management of Diabetes or other medical conditions. Other embodiments may apply to process automation in other areas utilizing management workflow software.

In an embodiment, a computerized method for remote management of a client medical condition is presented, comprising the steps of: receiving a communication in a call center, the communication comprising an audio speech based at least in part on words spoken by a client and a representative; identifying one or more keywords from the audio based at least in part on an acoustic model; generating a conversation score by scoring each of the one or more keywords; determining whether the conversation score meets a predetermined threshold; and alerting the representative in the event the conversation score meets the predetermined threshold.

In another embodiment, a method for managing a client medical condition utilizing workflow management is presented, comprising the steps of: receiving a communication in a call center, the communication comprising an audio speech based at least in part on words spoken by a client and a representative; applying keyword spotting to the communication as the communication occurs using a computing device programmed with instructions to enable the computing device to spot one or more predetermined keywords; determining if said one or more keywords have been spotted; and triggering a work item for the representative if said one or more keywords have been spotted.

BRIEF DESCRIPTION OF THE DRAWINGS

FIG. 6 is an illustration of a sample database record.

FIG. 7 is an illustration of a sample database record.

DETAILED DESCRIPTION

Figure 1:
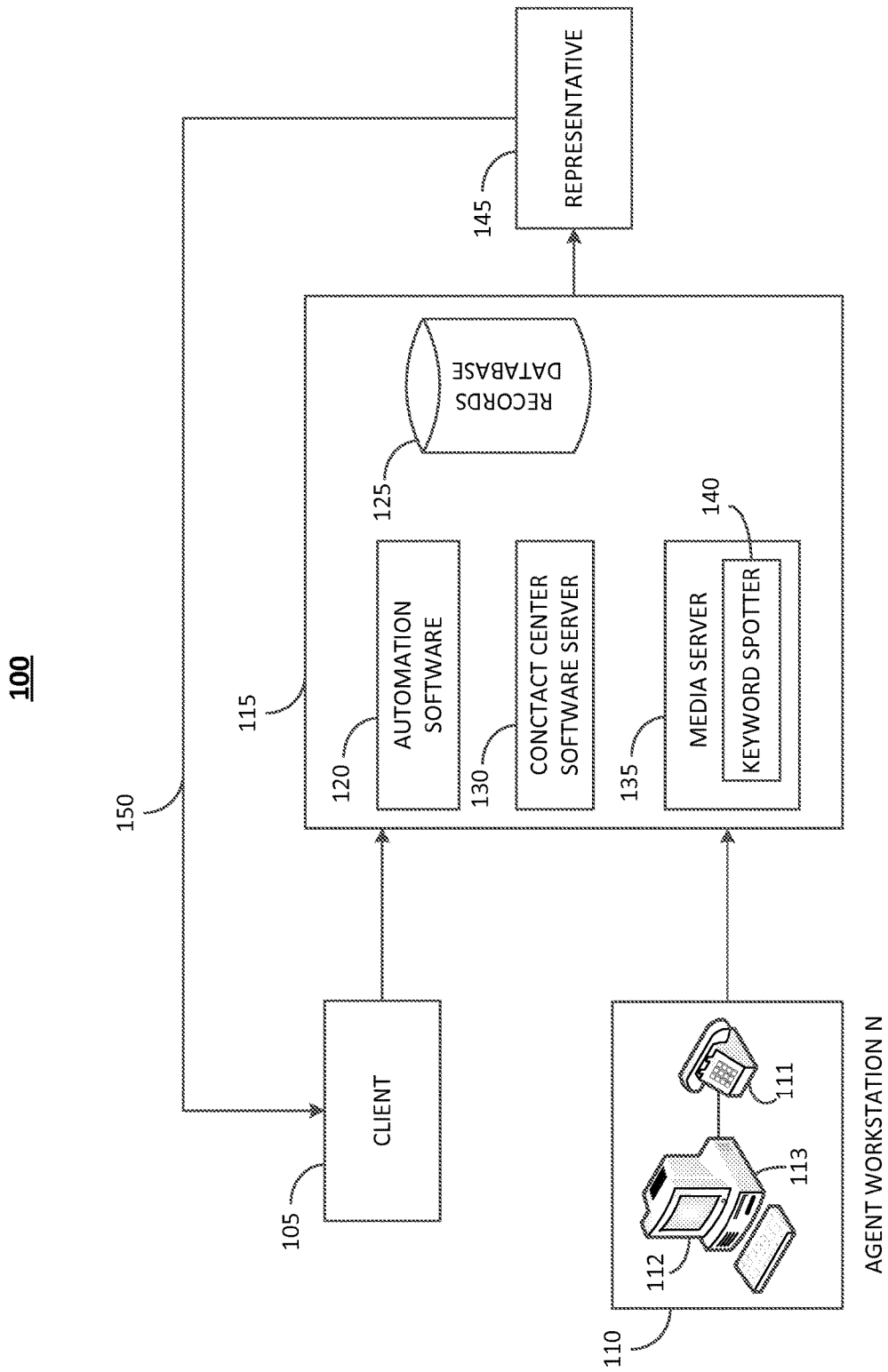
FIG. 1 is a diagram illustrating the basic components of an embodiment of a system.

For the purposes of promoting an understanding of the principles of the invention, reference will now be made to the embodiment illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Management workflow software may be applied within an organization to manage and define a series of tasks to produce a final outcome. Stages may be defined within the workflow such that a group or individual may be assigned to tasks within specific stages. Upon task completion, the system may notify those responsible for the next task and ensure uncompleted tasks are not forgotten. These types of systems are particularly useful in information-intensive industries and those with complex data-analysis.

In an embodiment, management workflow software may be combined with keyword spotting capabilities which is applied to communications. Keyword spotting may be used in conjunction with automatic speech recognition (ASR). ASR systems analyze human speech and translate them into text or words. The keyword spotter may be tuned to recognize industry specific keywords or any set of words desired by a user. Upon recognition of identified keywords, the workflow software may trigger an alert or action item that needs attention based on the communication. For example, a contact center may be set up to handle incoming communications from a person in regards to their health. An agent may handle the communications, which are being monitored for specific keywords. A person may speak the keywords, which may trigger an alert in the agent's display, for example, to let the agent know that a task needs completion. The person may be telling the agent about some symptoms they are having in the course of the communication, upon which the agent may receive an alert that the person might be a candidate in a monitoring program for their condition. The person may opt to enroll in the program and can then use the program to monitor their condition. In the event that the program detects unusual results, a professional or provider may be notified and can then contact the person. This may be particularly useful in remote areas where a person may not have access to a diverse staff of providers.

FIG. 1 is a schematic diagram illustrating the basic components of an embodiment of a system 100. The basic components of the system 100 may include: a Client 105; an Agent Workstation 110 which may comprise a Work Station Computer 113 coupled to a Display 112 and a Digital Telephone 111; a Network 115, which may comprise Automation Software 120, a Records Database 125, a Contact Center Software Server 130, and a Media Server 135, which may comprise a Keyword Spotter 140, and a Representative 145.

The Client 105 may be a person who is calling into the system 100 through the use of a POTN, cellular telephone networks, VoIP, etc., to name a few non-limiting examples.

For example, the Client 105 may comprise a patient who has a medical condition that may require ongoing care and monitoring. The Client 105 may enroll in the system 100 so that their medical condition may be monitored and information related to the medical condition may be gathered. The Client 105 may manually enter information pertaining to their medical condition into the system 100. Information may be entered via a device that is capable of transmitting data such as a telephone or a computer, to name some non-limiting examples. Medical information may also be automatically entered for monitoring of a medical condition or a potential medical condition.

The Agent Workstation 110 may include a Workstation Computer 113 coupled to a Display 112. It should be understood that while one Agent Workstation 110 is described in the illustrative embodiment, any number may be utilized. Contact center applications of system 100 typically include many more workstations of this type at one or more physical locations, but only one is illustrated in FIG. 1 to preserve clarity. Workstation Computers 113 may be of the same type, or a heterogeneous combination of different computing devices. Likewise, Displays 112 may be of the same type or a heterogeneous combination of different visual devices.

The Digital Telephone 111 may be associated with Agent Workstation 110. Additionally, the Digital Telephone 111 may be integrated into the Agent Computer 113 and/or implemented in software. It should be understood that the Digital Telephone 111, which is capable of being directly connected to the Network 115, may be in the form of handset, headset, or other arrangement as would occur to those skilled in the art. It shall be further understood that the connection from the Computer Network 115 to an Agent Workstation 110 can be made first to the associated workstation Digital Telephone 111, then from the workstation Digital Telephone 111 to the Workstation Computer 113 by way of a pass through connection on the workstation Digital Telephone 111. Alternatively, two connections from the Network 115 can be made, one to the workstation Digital Telephone 111 and one to the Workstation Computer 113. Although not shown to preserve clarity, the Agent Workstation 110 may also include one or more operator input devices such as a keyboard, mouse, track ball, light pen, and/or microtelecommunicator, to name just a few representative examples. Additionally, besides a Display 112, one or more other output devices may be included such as loudspeaker(s) and/or a printer, to name just a few representative examples. Agent Workstations 110, in at least one embodiment, may be located in a contact center which interacts with the Client 105 and/or the Representative 145.

The Network 115 may be in the form of a Computer Network comprising a Local Area Network (LAN), Municipal Area Network (MAN), Wide Area Network (WAN), such as the Internet, a combination of these, or such other network arrangement as would occur to those skilled in the art. The operating logic of system 100 can be embodied in signals transmitted over Network 115, in programming instructions, dedicated hardware, or a combination of these. It should be understood that any number of Workstation Computers 113 can be coupled together by the Network 115. The Network 115 may be connected with the Automation Software 120, the Records Database 125, the Contact Center Software Server 130, and the Media Server 135 which may comprise the Keyword Spotter 140

The Automation Software 120 may comprise a software suite. The software may be capable of optimizing processes through prioritizing and routing work to available workers at Agent Workstations 110 for timely completion. An example of Automation Software 120 may include Interaction Process Automation™ by Interactive Intelligence, Inc., for example, or any other process automation software.

The Records Database 125 may be a database capable of storing and organizing information. The Records Database 125 may comprise a medical records database of patient records, for example. In one embodiment, patient records may be those entered by the Representative 145, the Client 105, or be from any other source, and are monitored by the system 100. Patient records may comprise medical histories, biometrics, personal identifying information, or any other information.

The Contact Center Software Server 130 houses the software which operates a call center. It may be on-premise or cloud-based. An example of a Contact Center Software may include Interactive Intelligence, Inc.'s Customer Interaction Center™, or any other software which operates a contact center.

The Media Server 135 may store and share media within the Network 115. The Media Server 135 may also contain the Keyword Spotting module 140, an example of which is described in greater detail in FIG. 2.

The Representative 145 may comprise a person who is authorized to provide the Client 105 with advice or information. For example, the Representative 145 may comprise a healthcare provider who may reach out to a patient (i.e., the Client 105) in order to provide counsel related to a medical condition. Information input by patients may continue to be monitored by the Automation Software 120 through the Records Database 125 and the Network 115 as the Client 105 continues to update the system 100. In one embodiment, the Representative 145 may contact 150 the Client 105 via designated means, such as a telephone, e-mail, to name a few non-limiting examples, when the client information triggers an alert within the Network 115.

Figure 2:
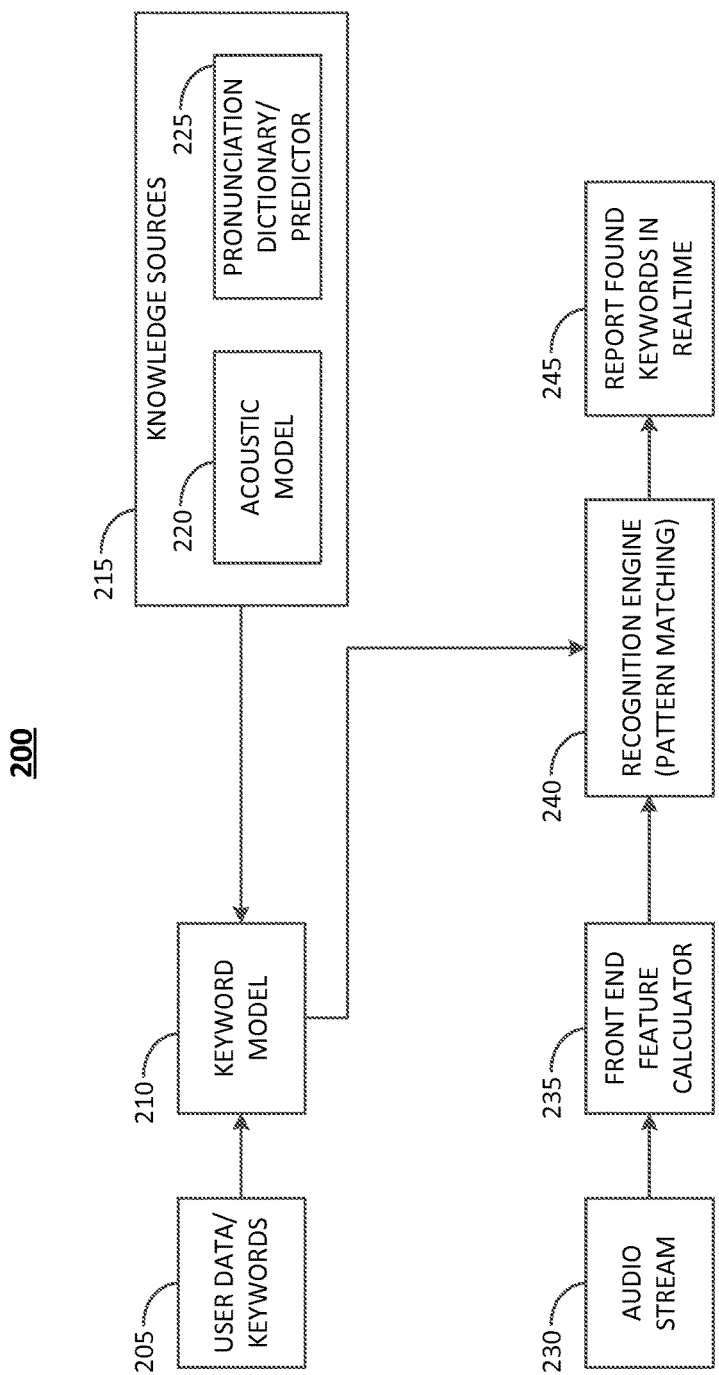
FIG. 2 is a diagram illustrating the basic components of an embodiment of a keyword spotting system.

FIG. 2 is a schematic diagram illustrating the basic components of an embodiment of a Keyword Spotter 200. The basic components of the Keyword Spotter 200 may include User Data/Keywords 205, Keyword Model 210, Knowledge Sources 215, which may include an Acoustic Model 220 and a Pronunciation Dictionary/Predictor 225, an Audio Stream 230, a Front End Feature Calculator 235, a Recognition Engine (Pattern Matching) 240, and the Reporting of Found Keywords in Real-Time 245.

User Data/Keywords 205 may be defined by the user of the system 200 according to user preference. The Keyword Model 210 may be formed by concatenating phoneme hidden Markov models (HMMs). The Keyword Model 210 may be composed based on the User Data/Keywords that are defined by the user and the input to the Keyword Model 210 based on Knowledge Sources 215. Such Knowledge Sources 215 may include the Acoustic Model 220 and the Pronunciation Dictionary/Predictor, 225.

The Knowledge Sources 215 may store probabilistic models of relations between pronunciations and acoustic events. The Knowledge Sources 215 may be developed by analyzing large quantities of audio data. The Acoustic Model 220 and the Pronunciation Dictionary/Predictor 225 are made, for example, by looking at a word like "hello" and examining the phonemes that comprise the word. Every Keyword 205 in the system 200 is represented by a statistical model of its constituent sub-word units called the phonemes. The phonemes for "hello" as defined in a standard phoneme dictionary are: "hh", "eh", "l", and "ow". Models of the four phonemes are then strung together into one composite model which then becomes the Keyword Model 210 for the world "hello". These Keyword Models 210 are language dependent. In order to also provide multi-lingual support, multiple Knowledge Sources 215 may be provided.

The Acoustic Model 220 may be formed by statistically modeling the various sounds that occur in a particular language. A phoneme is assumed to be the basic unit of sound. A predefined set of such phonemes is assumed to completely describe all sounds of a particular language. An HMM, which encodes the relationship of the observed audio signal and the unobserved phonemes, forms the fundamental theory for most modern speech recognition systems. A phoneme is considered to be composed of three states, representing the beginning, central, and trailing portions of the sound. An HMM is constructed by concatenating these three states. A training process studies the statistical properties of each of these states for all of the phonemes over a large collection of transcribed audio. A relation between the textual properties and the spoken properties is thus formed. Typically, the statistics of states may be encoded using a Gaussian mixture model (GMM). A set of these GMMs is termed as an acoustic model. Specifically, the one described in this application is referred to as a context-independent, or monophone, model. Many other model types may also be used. For example, many modern speech recognition systems may utilize a more advanced acoustic model, which may be context-dependent and capture the complex variations created due to the position of phonemes in conversational speech. Each state of a phoneme is specialized to its left and right neighboring phonemes. Clearly such a scheme would result in a very large number of GMMs in the acoustic model. One example of a context-dependent phoneme is a triphone.

The Pronunciation Dictionary 225 in FIG. 2 may be responsible for decomposing a word into a sequence of phonemes. Keywords 205 presented from the user may be in human readable form, such as grapheme/alphabets of a particular language. However, the pattern matching algorithm may rely on a sequence of phonemes which represent the pronunciation of the Keyword 205. A Pronunciation Dictionary 225 may store a mapping between commonly spoken words and their pronunciations. Once the sequence of phonemes is obtained, the corresponding statistical model for each of the phonemes in the Acoustic Model 220 may be examined. A concatenation of these statistical models may be used to perform keyword spotting for the word of interest. For words that are not present in the dictionary, a predictor, which is based on linguistic rules, may be used to resolve the pronunciations.

The Audio Stream 230 (i.e., what is spoken into the system by the user) may be fed into the Front End Feature Calculator 235, which may convert the Audio Stream 230 into a representation of the Audio Stream 230, or a sequence of spectral features. Audio analysis may be performed by segmenting the audio signal as a sequence of short (typically 10 ms) windows and extracting spectral domain features.

The Keyword Model 210 which may be formed by concatenating phoneme HMMs, and the signal from the Audio Stream 230 may both then be fed into a Recognition Engine for Pattern Matching 240. The task of the Recognition Engine 240 may be to take a set of Keyword Models 210 and search through the presented Audio Stream 230 to find if the words were spoken. In the multi-dimensional space constructed by the Front End Feature Calculator 235, a spoken word may become a sequence of Mel-Scale Frequency Cepstral Coefficient (MFCC) vectors forming a trajectory in the acoustic space. Keyword spotting may now simply become a problem of computing the probability of generating the trajectory given the Keyword Model 210. This operation may be achieved by using the well-known principle of dynamic programming, specifically the Viterbi algorithm in one embodiment, which aligns the Keyword Model 210 to the best segment of the audio signal, and results in a match score. If the match score is significant, the keyword spotting system 200 infers that the Keyword 205 was spoken and reports a keyword spotted event.

The resulting spotted Keywords 205 may then be reported in real-time, 245. The report may be presented as a start and end time of the Keyword 205 in the Audio Stream 230 with a confidence value that the Keyword 205 was found. The primary confidence value may be a function of how the Keyword 205 is spoken. For example, in the case of multiple pronunciations of a single word, the Keyword 205 "tomato" may be spoken as "te-mah-toh" and "te-may-toh". The primary confidence value may be lower when the word is spoken in a less common pronunciation or when the word is not well enunciated. The specific variant of the pronunciation that is part of a particular recognition is also displayed in the report.

Figure 3:
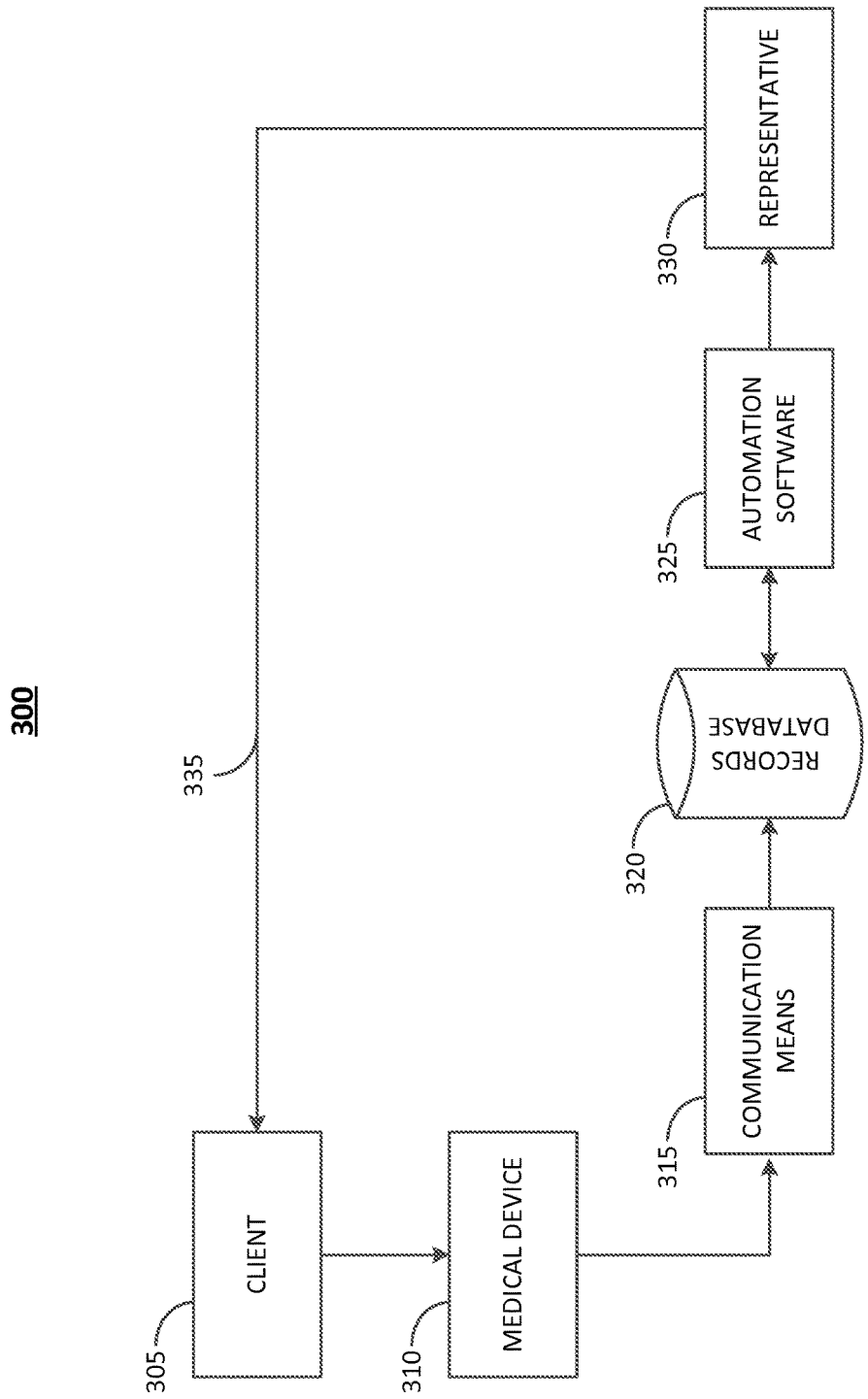
FIG. 3 is a diagram illustrating the basic components of an embodiment of a system.

FIG. 3 is a schematic diagram illustrating the basic components of an embodiment of a system 300. The basic components of the system 300 may include: a Client 305, a Medical Device 310, Communication Means 315, a Medical Records Database 320, Automation Software 325, and a Representative 330.

The Client 305 may be a person who is calling into the system 100 through the use of a POTN, cellular telephone networks, VoIP, etc., to name a few non-limiting examples. For example, the Client 305 may comprise a patient who has a medical condition that may require ongoing care and monitoring, such as Diabetes. The Client 305 may enroll in the system 300 so that their medical condition may be monitored and information related to the medical condition may be gathered. The Client 305 may manually enter information pertaining to their medical condition into the system 300. Information may also be automatically entered for monitoring of a medical condition or a potential medical condition.

The Medical Device 310, or other means for monitoring the medical condition of the Client 305, may interact with the Client 305 and the Communication Means 315. In one embodiment, the Medical Device 310 may comprise a glucose meter that measures the blood glucose content of a patient. Data may be entered into the Records Database 320 via the Communication Means 315. The Communication Means 315 may include any device that is capable of communication between the Client 305 and/or Medical Device 310 and the Records Database 320. For example, Communication Means 315 may include a computer or a telephone, or any device that is capable of transmitting data, where the Client 305 inputs information from the Medical Device 310, such as a blood glucose reading.

The Records Database 320 may be a database capable of storing and organizing information. The Records Database 320 may comprise a medical records database of patient records, for example. In one embodiment, patient records may be those entered by the Representative 330, the Client 305, or be from any other source, and are monitored by the system 300. Patient records may comprise medical histories, biometrics, personal identifying information, etc.

The Automation Software 325 may comprise a software suite. The software may be capable of optimizing processes through prioritizing and routing work to available workers for timely completion. An example of Automation Software may include Interaction Process Automation™ by Interactive Intelligence, Inc., or any other process automation software. The Automation Software 325 may interact with the Records Database 320 and the Representative 330.

The Representative 330 may comprise a person who is authorized to provide the Client 305 with advice or information. For example, the Representative 330 may comprise a healthcare provider who may reach out to a patient in order to provide counsel on a condition. Information input by patients may continue to be monitored by the Automation Software 325 through the Records Database 320 as the Client 305 continues to update the system 300. In the event where the client information triggers an alert, the Representative 330 may contact 335 the Client 305 via designated means, such as a telephone, e-mail, etc., to name a few non-limiting examples.

Figure 4:
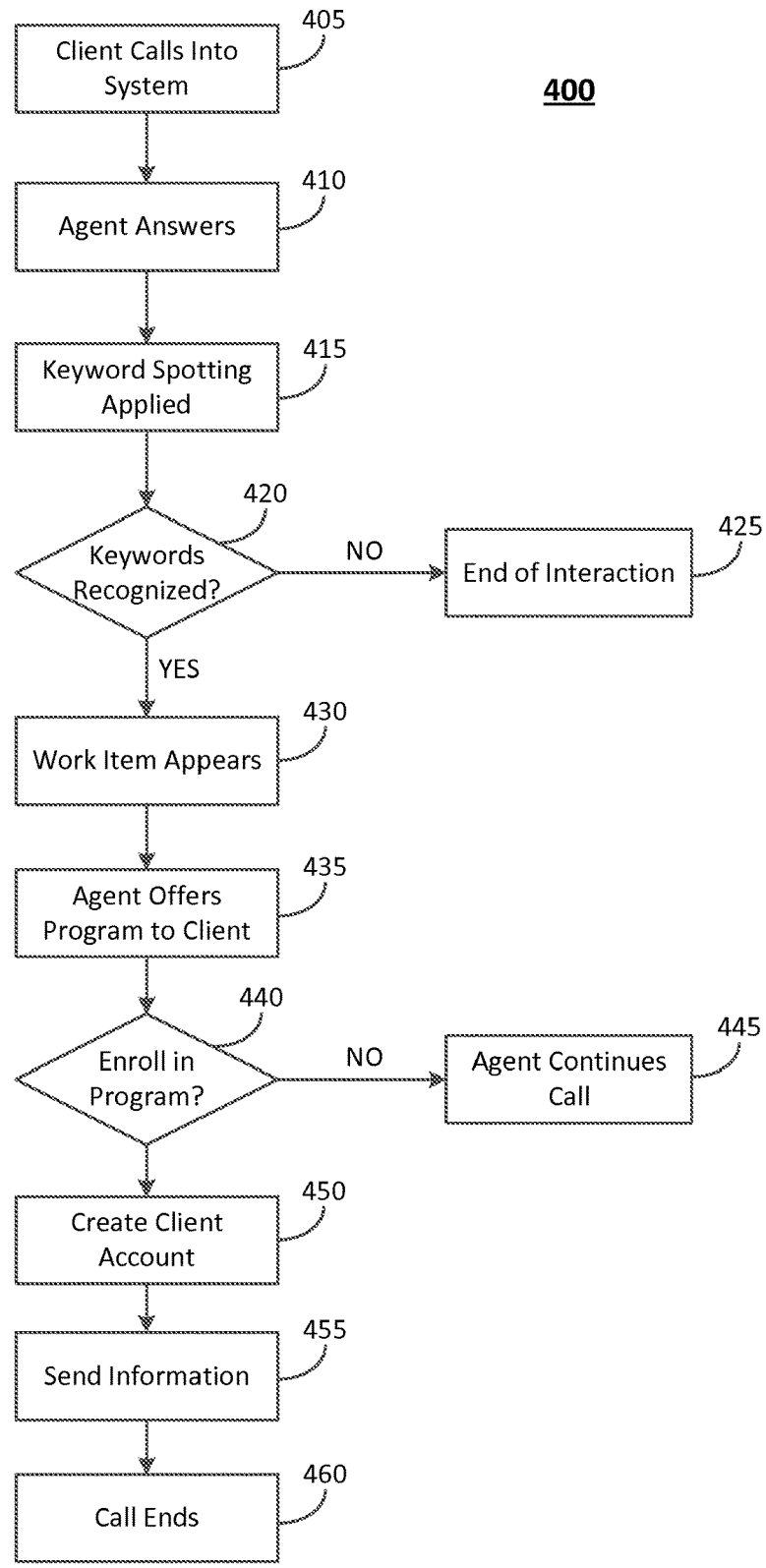
FIG. 4 is a flowchart illustrating an embodiment of a process with key word spotting applied.

FIG. 4 is a flowchart schematically illustrating an embodiment of a process 400 utilizing keyword spotting. The process 400 may be operative in the system 100 (FIG. 1). In one embodiment, for example, a person may contact the system 100 by calling in and interacting with the contact center agent. Keyword spotting 200 may be applied to the interaction to determine if the person may meet requirements to be enrolled in a monitoring program. Depending upon whether any keywords may be recognized, work items or alerts may be triggered to inform the contact center agent in real time that the person they are interacting with may be eligible for enrollment.

In operation 405, a client calls into the system. For example, a client may not feel well and place a call into a contact center to speak with an agent about their symptoms. A call center, in one embodiment, may be a healthcare facility. Control is passed to operation 410 and process 400 continues.

In operation 410, an agent answers the call. For example, the agent may be working in a call center, using workflow management software, such as Interaction Process Automation™ by Interactive Intelligence, Inc. The agent may begin a dialogue with the client about medical symptoms the client may be experiencing. Control is passed to operation 415 and process 400 continues.

In operation 415, keyword spotting 200 is applied to the communication. In at least one embodiment, the processing by the Keyword Spotter 200 may occur in real time. During a call, for example, the client, who may be a patient describing their symptoms to a healthcare facility agent, may use words that have been designated as Keywords 205 to trigger an alert by the system. A patient may communicate, "I have a dry-mouth and do not feel well. I am dizzy and I have a high sugar reading". The words "dry-mouth", "dizzy", and "high sugar" may be Keywords 205 that indicate the patient is having a medical issue. A Keyword Spotter 200, as described in FIG. 2, may detect these Keywords 205 during the conversation. Any type or number of Keywords 205 may be used and targeted towards a specific condition or field that the system is used in, such as in the medical field, insurance field, or any other field. Control is passed to operation 420 and process 400 continues.

In operation 420, it is determined whether or not any Keywords 205 have been recognized. If it is determined that Keywords 205 have not been recognized, control is passed to operation 425 and the process 400 continues. If it is determined that Keywords 205 have been recognized, control is passed to operation 430 and process 400 continues.

The determination in operation 420 may be made based on any suitable criteria. For example, the Keyword Spotter 200 may recognize keywords such as "dry-mouth", "dizzy", and "high sugar". These words may have been previously chosen for system recognition. A score may be assigned based on how many Keywords 205 or what type of Keywords 205 are spoken by the client or other party to the interaction. A predetermined threshold may trigger an alert for enrollment or some other action if the score meets the threshold. For example, the Keyword Spotter 200 may tally a score during the patient's call into the system. As the patient speaks, a value is assigned to any Keywords 205 associated with a specified condition. The more Keywords 205 that a patient speaks, the higher their score may be. As the score tallies, it may approach the threshold. In the event that a score exceeds the threshold, the system may trigger an alert to the agent to make an offer to the customer to enroll in the program based on Keywords 205 being identified in their dialogue. The score may be measured in real time as a party speaks. In at least one embodiment, spotting of a particular Keyword or Keywords 205 may trigger an alert or message.

In operation 425, the client interaction has ended as no Keywords 205 were recognized by the system. The process 400 ends.

In operation 430, a work item appears. In at least one embodiment, the score determined by Keywords 205 spoken by the client may trigger a work item to be sent to the agent. In another embodiment, Keyword(s) 205 may trigger a work item to appear to the agent. The work item may notify the agent that the client is a candidate for the program. For example, a notice may appear on the agent's display in the Agent Workstation 110. Control is passed to operation 435 and process 400 continues.

In operation 435, an agent offers a program to client. In one embodiment, this may be done during the interaction between the agent and the client. The agent may inform the client of the monitoring program and their candidacy based on the interaction. Control is passed to operation 440 and process 400 continues.

In operation 440, it is determined whether or not the client wishes to be enrolled in the system. If it is determined that the client does not wish to be enrolled in the system, control is passed to operation 445 and the process 400 continues. If it is determined that the client wishes to be enrolled in the system, control is passed to operation 450 and the process 400 continues.

The determination in operation 440 may be made based on any suitable criteria. For example, the client may have the option to say "yes" or "no" in response to being asked if they would like to be enrolled.

In operation 445, the client has opted out of the enrollment process, the agent continues the call, and the process 200 ends.

In operation 450, a client account is created. For example, the client may be asked for identifying information that is entered into the system. Identifying information may include any type of unique information such as the caller's full name, birthdate, address, gender, etc. This information may be assigned a unique identifier that may be used as a reference within the system. Control is passed to operation 455 and the process 400 continues.

In operation 455, information is sent to the client. In one embodiment, the client may receive an e-mail with a hyperlink that they can click on in order to enroll in the system and/or access their account. Control is passed to operation 460 and the process 400 continues.

In operation 460 the call ends and the process 400 ends.

Figure 5:
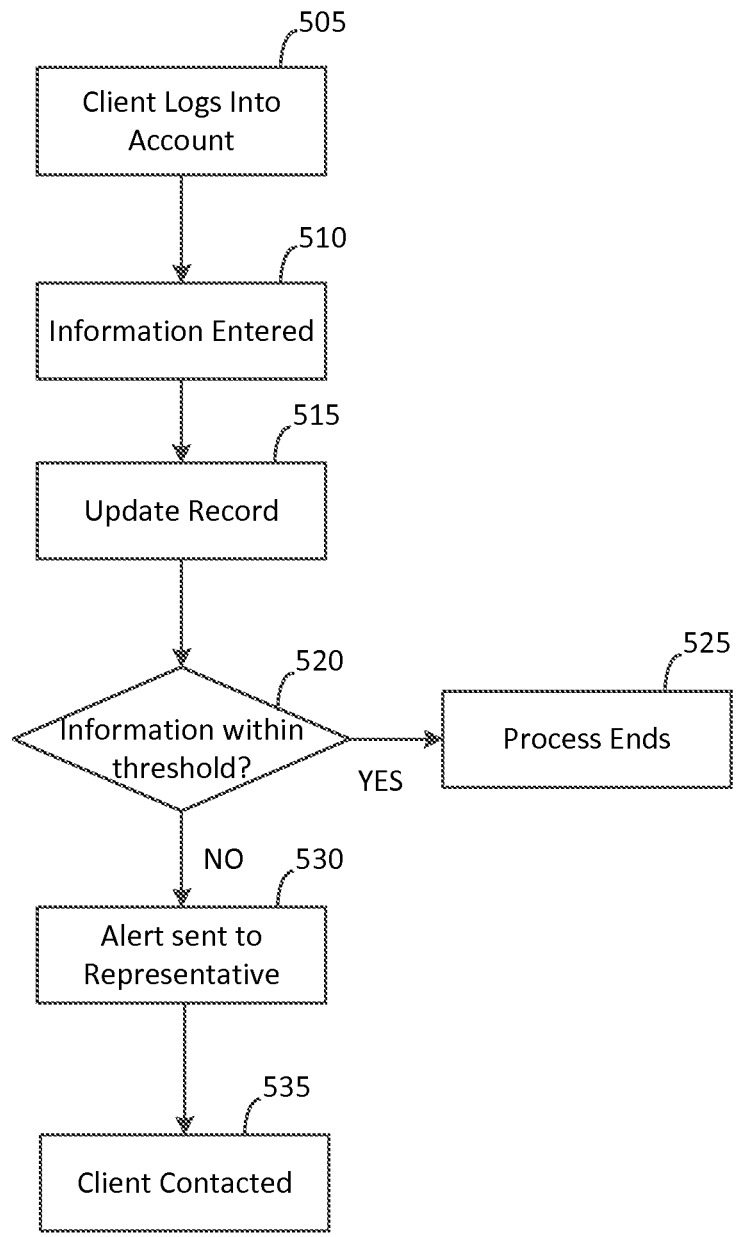
FIG. 5 is a flowchart illustrating an embodiment of a process for managing client information.

FIG. 5 is a flowchart illustrating an embodiment of a process for managing client information. The process 500 may be operative in the system 100 (FIG. 1).

In operation 505, a client accesses their account. For example, the client may log onto their account through a website on their computer. Other methods may be utilized to access accounts, such as through a smart phone application, for example. In another embodiment, any device that can transmit data may be used to access accounts. In another embodiment, a work item may be sent for completion to the client through process automation software. Control is passed operation 510 and the process 500 continues.

In operation 510, client information is entered. Client information may be any type of data for monitoring by the system. For example, a reading from the patient's medical device may be input into the record. This may be done manually or automatically, such as by being uploaded by the patient's medical device that is operably coupled to the system for data transmission. The patient's device, such as a blood glucose meter, may return a glucose reading of 300 mg/dL which is input into the record, for example. Control is passed to operation 515 and the process 500 continues.

In operation 515, the client record is updated. For example, the glucose reading of 300 mg/dL from the patient's medical device may be added to records of past glucose readings to complete a patient history. Control is passed to operation 520 and the process 500 continues.

In operation 520, it is determined whether or not the information is within the predetermined threshold. If it is determined that the information is within the threshold, control is passed to operation 525 and the process 500 continues. If it is determined that the information is not within the threshold, control is passed to operation 530 and the process 500 continues.

The determination in operation 520 may be made based on any suitable criteria. In one embodiment, each client may have a previously determined threshold for their information type, such as a blood glucose reading equal to or greater than 300 mg/dL for a Diabetic. This threshold may help the system determine whether the client's readings are high, low, or within their manageable range. A reading that falls outside of the threshold may trigger an alert to a health care provider that the patient needs counseling on their condition.

In operation 525, the information is within the threshold and an alert has not been sent. The process 500 ends.

Figure 8:
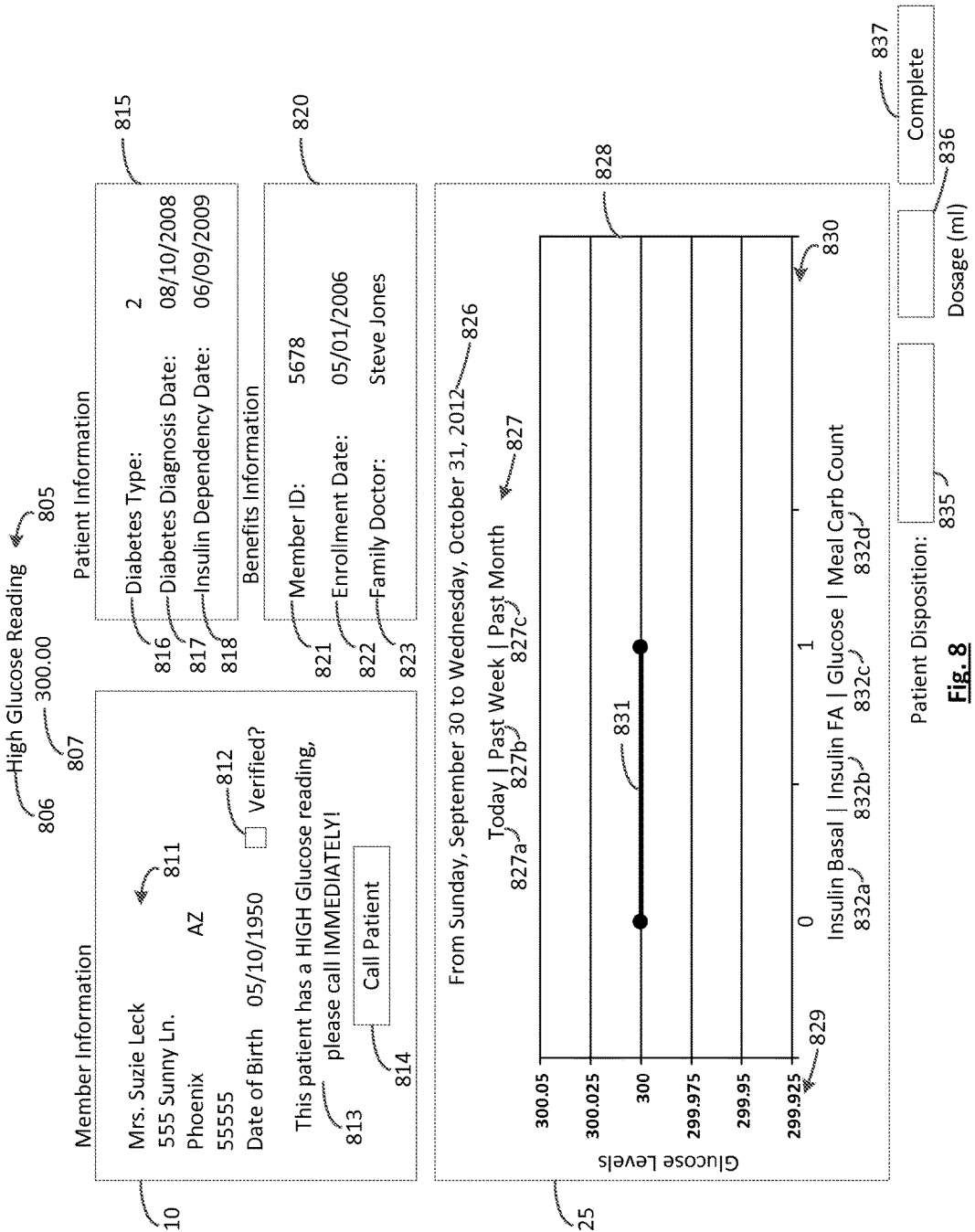
FIG. 8 is an example of an embodiment of a Guided User Interface.

In operation 530, a message is sent to the representative to contact the client. For example, an alert may appear on a health care provider's computer in the form of the GUI 800 (FIG. 8). The alert may indicate that the patient has unusually high blood sugar. This alert may notify the provider that action needs to be taken and to follow up with the client. Control is passed to operation 535 and the process 500 continues.

In operation 535, the client is contacted. For example, a healthcare provider may use the information from the patient's account to contact the patient. Contact may occur via telephone or any other suitable means that have been specified. The process 500 ends.

In one embodiment, a client may be contacted if an agent or representative notices that there has been no activity in a client's account for a period of time. A client may be reminded to enter information into the system. As another example, if no activity is noticed after a period of time, the client may have died and the account should be de-activated.

FIG. 6 is an illustration of a sample database record which may contain client information. The sample database record may comprise a number of Client Information Records 600. While only a few sample records, 600a, 600b, and 600c, have been illustrated in FIG. 6, any number of Client Information Records 600 may be provided. A Client Information Record 600 may be associated with or resident in the Records Database 120 (FIG. 1). A Client Information Record 600 may comprise the following non-limiting exemplary fields: Date/Time Created 605, User ID 610, Date of Birth 615, Title 620, First Name 625, Last Name 630, Phone Number 635, Email 640, Gender 645, Smoker 650, Occupation 655, State 660, and Gross Annual Income 665.

The Date/Time Created field 605 may provide the information such as when a record was created. Using the example shown in FIG. 6, '1/5/2013 8:00:00 AM' is the Date/Time Created associated with the client information record 600a. '1/5/2013 at 8:00:00 AM' may indicate that the record was created at 8:00:00 AM on Jan. 5, 2013. The Date/Time Created field for record 600b has a value of '1/5/2013 10:32:00 AM' and the Date/Time Created field for record 600c has a value of '1/7/2013 2:53:00 PM'.

The User ID field 610 may provide unique user identification. For example, the User ID 610 may be a randomly generated alpha-numeric code or a character sprint. The User ID 610 may indicate an identifier that is used relevant to each account. Although particular examples of User IDs 610 are presented herein, any sort of unique identifier may be used without departing from the scope of the embodiments described herein. Using the example shown in FIG. 6, '5678' is the User ID 610 associated with the client information record 600a. '23504' is the User ID 610 associated with record 600b and '85213' is the User ID 610 associated with record 600c.

The Date of Birth field 615 may indicate the birthdate of the client. Data may be presented in a date format such as May 10, 1950 or 05/10/1950, or any other desired format. For example, '5/10/1950' is the Date of Birth 615 associated with the client information record 600a. The Date of Birth '8/6/1944' is the Date of Birth 615 associated with record 600b and '1/4/1979' is the Date of Birth 615 associated with record 600c.

The Title field 620 may indicate information about the client, such as marital status or a preference by the client as to what title they prefer to be called. Options may include Mr., Mrs., Ms., Dr., Miss, etc. Using the example shown in FIG. 6, 'Mrs.' is the Title 620 associated with the client information record 600a. 'Dr.' is the Title 620 associated with record 600b and 'Mr.' is the Title 620 associated with record 600c.

The First Name field 625 may indicate the first name of a client. Using the example shown in FIG. 6, 'Suzie' is the First Name 625 associated with the client information record 600a. 'Jim' is the First Name 625 associated with record 600b and 'Brian' is the First Name 625 associated with record 600c.

The Last Name field 630 may indicate the last name of a client. Using the example shown in FIG. 6, 'Leck' is the Last Name 630 associated with the client information record 600a. 'Doe' is the Last Name 630 associated with record 600b and 'Parsons' is the Last Name 630 associated with record 600c.

The Phone Number field 635 may indicate contact information for a client. The format of a Phone Number 635 may be in any format or length. The examples shown in FIG. 6 are in US format. Using the example shown in FIG. 6, '555-555-5555' is the Phone Number 635 associated with the client information record 600a. '555-555-6645' is the Phone Number 635 associated with record 600b and '555-555-1235' is the Phone Number 635 associated with record 600c.

The Email field 640 may indicate contact information for a client such as an electronic mail address. Using the example shown in FIG. 6, 'suzieleck234@isp.com' is the Email 640 associated with the client information record 600a. The data 'none' is contained in the Email 640 field associated with record 600b, which may indicate that the there is no Email address associated with the client information record 600b. The data captain@isp.com' is the Email 640 associated with record 600c.

The Gender field 645 may indicate the gender of the client. Gender 645 may be indicated in any manner, such as by an 'F' for Female or an 'M' for male and a 'U' for unknown, for example. Using the example shown in FIG. 6, 'F' is the Gender 645 associated with the client information record 600a, which may indicate that the client associated with record 600a is a female. 'M' is the Gender 645 associated with records 600b and 600c.

The Smoker field 650 may provide information about whether or not the client is a smoker. This information may be indicated by a 'Y' or 'Yes' for Yes, for example. An 'N' or 'No' may indicate that the client is a non-smoker, for example. Using the example shown in FIG. 6, 'Yes' is associated with the Smoker field 650 of client information record 600a, indicating that the client is a smoker. The Smoker field 650 information 'N' is associated with records 600b and 600c, indicating that the clients are non-smokers.

The Occupation field 655 may provide information related to the occupation of the client. Using the example shown in FIG. 6, 'Homemaker' is the Occupation 655 associated with the client information record 600a. 'Retired' is the Occupation 655 associated with record 600b and 'Skilled Trade' is the Occupation 655 associated with record 600c.

The State field 660 may indicate the state of residence of a client. This information may be formatted in any manner, such as using standard abbreviations or in any other manner that may indicate the residency of the client. Using the example shown in FIG. 6, 'AZ' is the State 660 associated with the client information record 600a, indicating that the client resides in the state of Arizona. 'NV' is the State 660 associated with record 600b, indicating that the client resides in Nevada, and 'AK' is the State 660 associated with record 600c, indicating that the client resides in Alaska.

The Gross Annual Income field 665 may indicate a range or a general amount of the client's gross annual income. Using the example shown in FIG. 6, '$50,000' is the Gross Annual Income 665 associated with the client information record 600a. '$0' is the Gross Annual Income 665 associated with record 600b and '$45,000' is the Gross Annual Income 665 associated with record 600c.

FIG. 7 is an illustration of a sample database record which may contain client readings. The sample database record may comprise a number of client reading records 700. While only a few sample client reading records, 700a, 700b, and 700c, have been illustrated in FIG. 7, any number of client reading records 700 may be provided. A client reading record 700 may be associated with or resident in the Records Database 120 (FIG. 1). Each client reading record 700 may comprise the following non-limiting exemplary fields: User ID 705, Reading 710, Reading Type 715, Time of Reading 720, and Record Created 725.

The User ID field 705 may provide unique user identification. For example, the User ID 705 may be a randomly generated alpha-numeric code. The User ID 705 may indicate an unique identifier that is assigned to each account. Although particular examples of User IDs 705 are presented herein, any type of unique identifier may be used without departing from the scope of the embodiments disclosed herein. Using the example shown in FIG. 7, '5678' is the User ID 705 associated with the client reading record 700a. '23504' the User ID 705 is associated with record 700b and '85213' is the User ID 705 associated with record 700c.

The Reading field 710 may provide medical information about a client. The Reading 710 may be from a Glucose meter, a meal carb count, or an insulin basal dose, to name just a few non-limiting examples. The information in the Reading field 710 may be input by the client manually or provided automatically, such as by a medical device operatively coupled to the system 100 for transfer of information thereto. Using the example shown in FIG. 7, '300' is the Reading 710 associated with the client reading record 700a. '150' is the Reading 710 associated with record 700b and '129' is the Reading 710 associated with record 700c.

The Reading Type field 715 indicates the type of reading used to obtain the information in the Reading field 710. The Reading Type 715 may include 'Insulin Basal', 'Glucose', 'Meal Carb Count', etc., to name just a few non-limiting examples. Using the example shown in FIG. 7, 'Glucose' is the Reading Type 715 associated with the client reading records 700a and 700b, while HDL is the Reading Type 715 associated with the client reading record 700c.

The Time of Reading field 720 may indicate the date and/or the time that the Reading 710 was taken by the client. Using the example shown in FIG. 7, '1/5/2013 7:59:00 AM' is the Time of Reading 720 associated with the client reading record 700a. The Time of Reading 720 for record 700b has a value of '1/4/2013 05:17:00 PM' and the Time of Reading 720 for record 700c has a value of '1/7/2013 2:52:00 PM'.

The Record Created field 725 may indicate the date and/or the time that the client reading record 700 was created. Using the example shown in FIG. 7, '1/5/2013 8:00:00 AM' is the Record Created 725 associated with the client reading record 700a. '1/5/2013 at 8:00:00 AM' may indicate that the record was created at 8:00:00 AM on Jan. 5, 2013. The Record Created 725 for record 700b has a value of '1/5/2013 10:32:00 AM' and the Record Created 725 for record 700c has a value of '1/7/2013 2:53:00 PM'.

FIG. 8 is an example of an embodiment of a Graphical User Interface (GUI) 800. A Guided User Interface 800 may be presented to a Representative 130 in the event that an alert is triggered by the system. The Guided User Interface 800 may contain identifying information of a client, history, and information that is triggering an alert.

A heading 805 may be present on the GUI 800. This heading 805 may contain information pertinent to the window being displayed to the Representative 130. Using the example shown in FIG. 8, a 'High Glucose Reading' 806 appears in the heading 805 along with the reading '300', 807. This information may indicate to a healthcare Representative 130 that a patient has a high glucose reading and it is '300'. The Representative 130 can read this information to understand what the alert is for. Block 810 may contain member information about the client. Member Information may include the client's name, address, a birthday, etc., 811. Contact information may also be present. A check box may be present 812, to indicate if the information is verified as current or if the Representative 130 needs to update this information. An alert 813 may appear that indicates why the Representative 130 received a notification. In FIG. 8, the alert 813 indicates "This patient has a HIGH Glucose reading, please call IMMEDIATELY!" This information may inform the Representative 130 about the medical condition that triggered the alert and enable the Representative 130 to provide informed counseling.

The patient information window 815 may contain medical information about the patient. For example, such information may include the diabetes type 816, the diabetes diagnosis date 817, and the insulin dependency date 818. Using the example shown in the patient information window 815, the patient has type 2 Diabetes. The patient was diagnosed on Aug. 10, 2008 and insulin dependency began on Jun. 9, 2009. Medical Information may provide the Representative 130 with a brief history about the patient's medical condition, for example.

Other useful information may be provided in the GUI, such as the benefits information window 820. The benefits information window 820 may contain such information as an identification number 821, the enrollment date in the benefits 822, and the name of a primary care physician 823.

The patient window 825 may indicate a history of patient readings and types that can aid the Representative 130 in their consultation. In field 826, a range is given to indicate when the displayed readings were taken. In the example of FIG. 8, the field 826 indicates that readings are provided in the range 'From Sunday, September 30 to Wednesday, Oct. 31, 2012'. Field 827 may indicate links that a provider can click on to display results from different time frames, such as "today" 827a, "past week" 827b, and "past month" 827c.

A graph 828 may provide a visual display of the information with plots indicating the reading number 830 and the glucose levels 829 for that reading. Links 832 may be provided which indicate the reading types that are displayed in the graph 828. These types may include insulin basal 832a, insulin FA 832b, glucose 832c, and meal carb count 832d. This information may vary depending on the type of condition. For example, a cholesterol GUI 800 might include triglycerides with HDL measurements, LDL measurements, and lipid profiles.

Additional fields in the GUI 800 may indicate the outcome of the Representative 130's consultation with the client, such as the Patient Disposition field 835 and the dosage (ml) 836 of insulin that was recommended to the patient. A complete button 837 may be available for the Representative 130 to click on, indicating that the incident has been resolved.

While the invention has been illustrated and described in detail in the drawings and foregoing description, the same is to be considered as illustrative and not restrictive in character, it being understood that only the preferred embodiment has been shown and described and that all equivalents, changes, and modifications that come within the spirit of the invention as described herein and/or by the following claims are desired to be protected.

Hence, the proper scope of the present invention should be determined only by the broadest interpretation of the appended claims so as to encompass all such modifications as well as all relationships equivalent to those illustrated in the drawings and described in the specification.

The invention claimed is:

1. A method for detecting a patient medical condition utilizing a media server, the method comprising:
   receiving, by the media server, biometrics and medical history information from a medical device that is monitoring the medical condition of the patient, over a computer network;
   storing the received biometrics and medical history information in a data record having a data structure comprising of User ID, Reading that includes medical information about the patient, Reading Type that indicates a type of the medical information, and a Time of Reading;
   receiving an audio communication by the media server, the audio communication comprising an audio speech based at least in part on words spoken by the patient and a representative, wherein the audio communication is automatically initiated based on information monitored by the medical device and the stored data structure;
   segmenting the audio speech as a sequence of time windows and extracting spectral domain features from the time windows;
   generating keyword models from the spectral domain features;
   assigning a score to each word spoken by the patient that matches a keyword model, wherein as the patient speaks, a higher score is assigned to a word spoken by the patient that matches a keyword model when said word is repeated by the patient;
   detecting, by the media server, one or more keywords in the audio speech when the score of said one or more keywords exceeds a predetermined threshold;
   triggering an electronic message with instructions for an action, wherein the electronic message is based on information monitored by the medical device and the keywords recognized by the media server; and
   displaying the electronic message on a display.

2. The method of claim 1, wherein said representative comprises a healthcare provider.

3. The method of claim 1, further comprising enrolling the patient into a monitoring program by creating an account when said one or more keywords have been detected.

4. The method of claim 3, wherein the enrolling further comprises setting workflow rules and thresholds, wherein the audio communications is further initiated based on the rules and the thresholds.

5. The method of claim 3, further comprising:
   accessing the account by the patient and inputting information into said account;
   determining if the information meets a threshold; and
   sending an alert to the representative to contact the client.

6. The method of claim 5, wherein the representative accesses a Graphical User Interface for information related to one or more of: the patient and the alert.

* * * * *